United States Patent
Ko et al.

(10) Patent No.: US 6,718,817 B1
(45) Date of Patent: Apr. 13, 2004

(54) SAMPLE INJECTION DEVICE FOR GAS CHROMATOGRAPHY

(75) Inventors: Hsien-Wen Ko, Taoyuan (TW); Wun-Shung Lee, Taipei (TW); Fu-Hsiang Wang, Taipei (TW); Jon-Wey Chu, Shin-Chu (TW)

(73) Assignee: Chung-Shan Institute of Science and Technology, Lung-tan (TW)

( * ) Notice: Subject to any disclaimer, the term of this patent is extended or adjusted under 35 U.S.C. 154(b) by 0 days.

(21) Appl. No.: 10/301,750

(22) Filed: Nov. 22, 2002

(51) Int. Cl.[7] .......................... G01N 30/04; G01N 1/20
(52) U.S. Cl. .................................... 73/23.42; 73/863.71
(58) Field of Search .......................... 73/23.42, 23.22, 73/23.35, 23.4, 23.41, 863.71; 96/101; 156/89.11; 216/10; 250/281; 417/413.2, 566

(56) References Cited

U.S. PATENT DOCUMENTS

| | | | | |
|---|---|---|---|---|
| 4,471,647 A | * | 9/1984 | Jerman et al. | 73/23.4 |
| 4,895,500 A | * | 1/1990 | Hok et al. | 417/566 |
| 4,935,040 A | * | 6/1990 | Goedert | 73/23.22 |
| 5,277,556 A | * | 1/1994 | van Lintel | 417/413.2 |
| 5,313,061 A | * | 5/1994 | Drew et al. | 250/281 |
| 5,487,313 A | * | 1/1996 | Johnson | 73/863.71 |
| 5,583,281 A | * | 12/1996 | Yu | 73/23.42 |
| 6,068,780 A | * | 5/2000 | Yu | 216/10 |
| 6,454,840 B1 | * | 9/2002 | Gellert et al. | 96/101 |
| 6,457,347 B1 | * | 10/2002 | Koo et al. | 73/23.35 |
| 6,527,890 B1 | * | 3/2003 | Briscoe et al. | 156/89.11 |
| 6,575,014 B2 | * | 6/2003 | Lo et al. | 73/23.41 |

* cited by examiner

Primary Examiner—Hezron Williams
Assistant Examiner—Jay L Politzer
(74) Attorney, Agent, or Firm—Troxell Law Office PLLC

(57) ABSTRACT

The present invention herein relates to a sample injection device for micro gas chromatograph is assembled from five layers of thin plates and membrane. The first layer serves as cover plate and interfacial connection to outside columns. The second layer is fabricated with a sample channel and a carrier gas inlet split into an analytical channel and a reference gas channel, and two valve seats. The third layer is a flexible diaphragm for valve actuation. The fourth layer is fabricated with a pressurizing gas inlet hole and pressurizing channel leading to the diaphragms of valve seats. The fifth layer serves as another cover plate. An external solenoid valve is used to control the processes of sampling and injection. The channels and valve seats on each layer plate can be fabricated through several well-developed fabrication techniques such as photolithographic, LIGA processes or precision micro machining. All five layers are properly aligned and bonded by adhesives.

21 Claims, 10 Drawing Sheets

SAMPLE INJECTION DEVICE FOR GAS CHROMATOGRAPHY

REFERENCE CITED

1. U.S. Pat. No. : 4,471,647
2. U.S. Pat. No. : 4,935,040
3. U.S. Pat. No. : 4,869,282
4. U.S. Pat. No. : 5,487,313
5. U.S. Pat. No. : 5,652,398

FIELD OF THE INVENTION

The present invention relates to a sample injection device, particularly to require only one external control solenoid valve to activate three micro valves in corresponding application of gas chromatography. Therefore, this invention can be employed a much less pressure process with sample injector.

BACKGROUND OF THE INVENTION

In general, gas chromatograph is the most widely used instrument for analysis of gas mixtures. A gas chromatograph include three major components: an analytical column which physically separates the components of the mixture, a detector which senses the individual component after separation, and an injector which introduces a fix amount of gas sample and carried to analytical column by carrier gas. The most conventional injection techniques are syringe and sample loop methods. The later includes a six-port rotary valve, in which the sample is first introduced into the loop while a carrier gas flows to the analytical column through channels in this device. When the rotor is turned into a proper position, usually one-sixth of a turn, the sample loop becomes part of the channel that conducts the carrier gas into the analytical column. Therefore, the sample is swept into the analytical column. In the recent decades, portable micro gas chromatograph has attracted much attention. A palm-size gas chromatograph has become a reality in recent years due to advances in lab-on-a-chip. This six-port rotary valve injector is slow in response, and very difficult to fabricate into a miniature fixture for micro gas chromatograph. In addition, the rotary valve wears out easily. Apparently, it is not suitable for micro gas chromatograph.

There have been several designs for micro-machined injector In existence. They usually contain several micro valves each connected to a solenoid valves for control, separately. U.S. Pat. No. 5,487,313, entitles "Fluid-lock fixed volume injector" issued on Jan. 30, 1996, and incorporated by references herein, describes a sample injection scheme which requires pressurization and storage of the gas sample in a chamber up to 80 psi, and then inject a fixed amount of sample by time opening the micro valve. Four valves confine the pressurized gas In the sample chamber. By so doing, the micro valves must be capable of withstanding such a high pressure without leaking. It requires many precisely controlled silicon micro fabrication steps. Besides, all these valves are activated by external controls independently.

To simplify these problems, we developed a novel design of sample injector, which requires only one external control solenoid valve to activate three micro valves in the injection system and much less pressure.

OBJECT OF THIS INVENTION

Due to the continuous development of chemical industry, requirement of instrument for analysis of gas mixtures is always important. Thus, the improvement of sample injection device is to be of great urgency.

Therefore, the main object of the present invention is to provide an external control solenoid valve to activate three micro valves in the injection system.

Another object of the present Invention is to reduce the production cost for a sample injection device.

SUMMARY OF THE INVENTION

Specifically, the present invention of a sample injection device for micro gas chromatograph is assembled from five layers of thin plates and membrane. The first layer serves as cover plate and interfacial connection to outside columns, The second layer is fabricated with a sample channel and a carrier gas inlet, which splits into an analytical channel and a reference gas channel, and t valve seats. The analytical gas channel and reference gas channel are much narrower than sample channel such that a proper pressure difference is generated between opposing sides of the diaphragm of injection valve upon introduction of pressurizing gas. The third layer is a flexible diaphragm for valve actuation. The fourth layer is fabricated with a pressurizing gas inlet hole and pressurizing channel leading to the diaphragms of valve seats. The fifth layer serves as another cover plate and a port is etched for connection to the pressurizing tube and carrier gas tank. An external solenoid valve is used to control the processes of sampling and injection. At the normal situation without actuating the solenoid valve, inlet valve and outlet valve are open but injection valve is closed. Sample is drawn into the sample channel by a pump. When the solenoid valve is actuated and gate open, channels are pressurized which leads to closing of inlet/outlet valves and opening of the injection valve so that a plug of sample is injected to the mixing channel and led to the analytical column. Amount of sample injection is controlled by the duration of solenoid valve opening, usually less than 1 second. The channels and valve seats on each layer plate can be fabricated through several well-developed fabrication techniques such as photolithographic, LIGA processes or precision micro machining. All five layers are property aligned and bonded by adhesives. This assembly forms a sound and workable sample injection device.

BRIEF DESCRIPTION OF THE DRAWINGS

The present invention will be better understood from the following detailed description of preferred embodiments of the invention, taken in conjunction with the accompanying drawings, in which.

DESCRIPTION OF THE PREFERRED EMBODIMENT

According to the disadvantages of conventional sample injector for gas chromatograph as described above, the present invention provides an improvement solution for that. Embodiments of this invention will be described in detail with reference to attached drawings. To distinguish the synonymous words channel, column and tube in this text, channel is used strictly only in the etched section of the wafer, column is used to describe the analytical and reference capillaries of the gas chromatograph and tube is referred to the connector to the gas tank.

Figure 1:
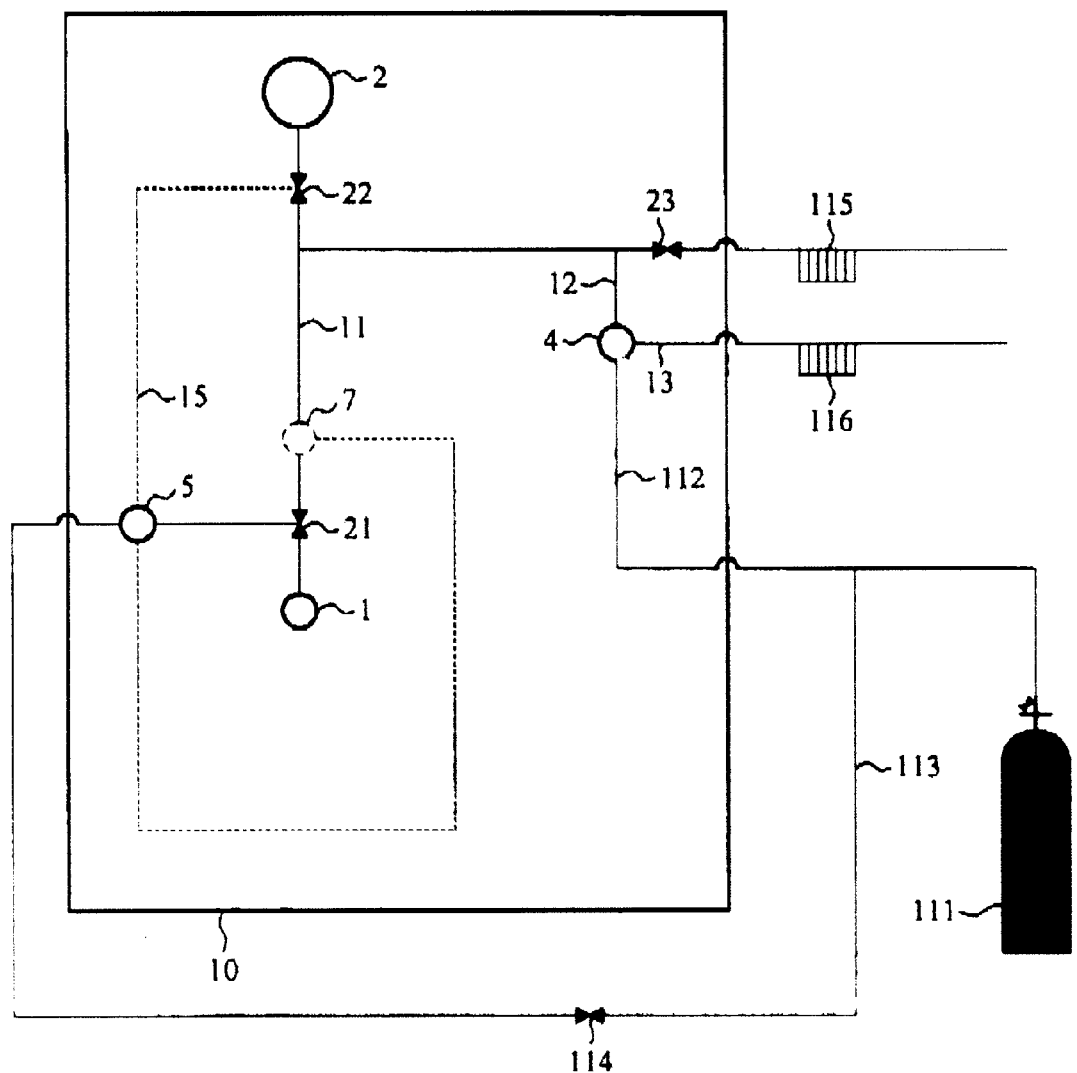
FIG. 1 shows the schematic view of gas chromatograph system with a sample injector in accordance with the present invention.

FIG. 1 shows the schematic view of gas chromatograph system with a sample injector in accordance with the present invention. The gas chromatograph includes a carrier gas tank 111, a gas injection device 10, an analytical capillary column and a reference capillary column both made of the sane material and available from commercial source. The ends of the capillary column are connected to a gas detector (not shown) to distinguish signals from different gaseous species.

Figure 2:
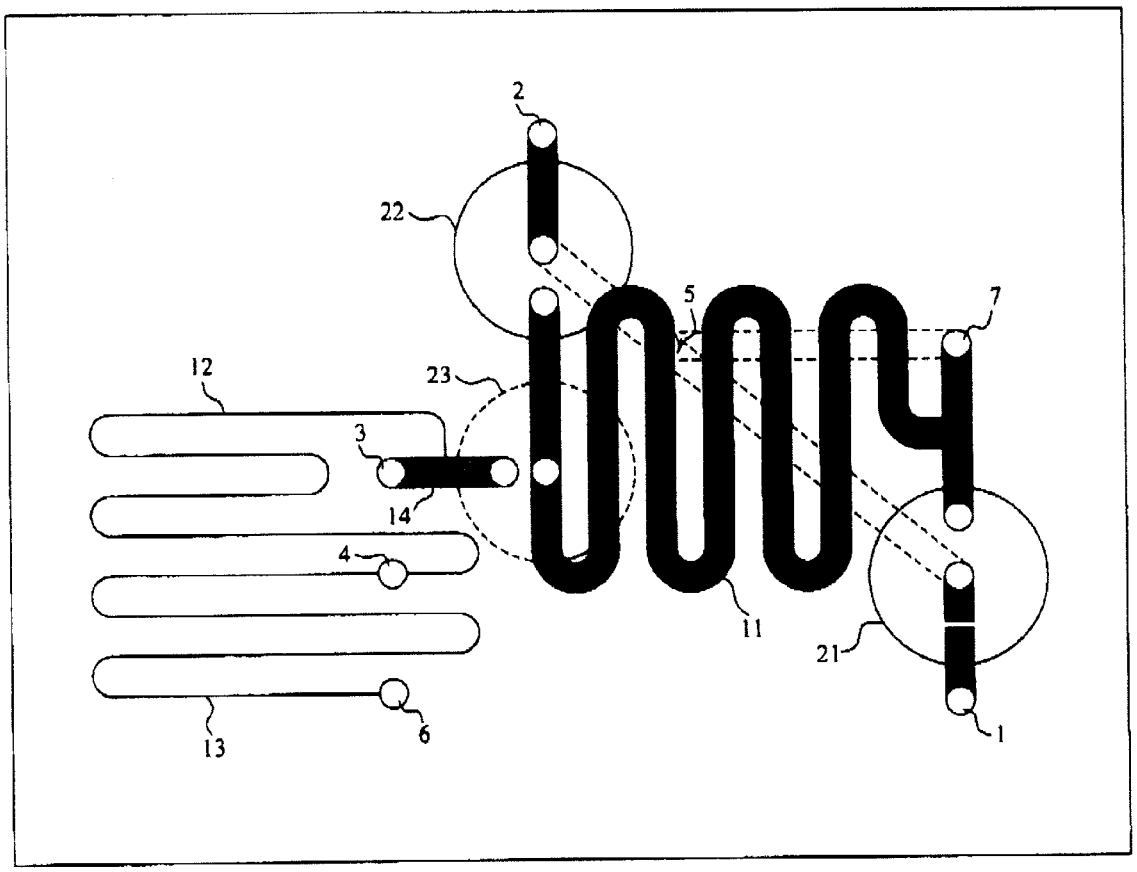
FIG. 2 shows the micro fabricated view of the injection assembly in accordance with the present invention.
Figure 3:
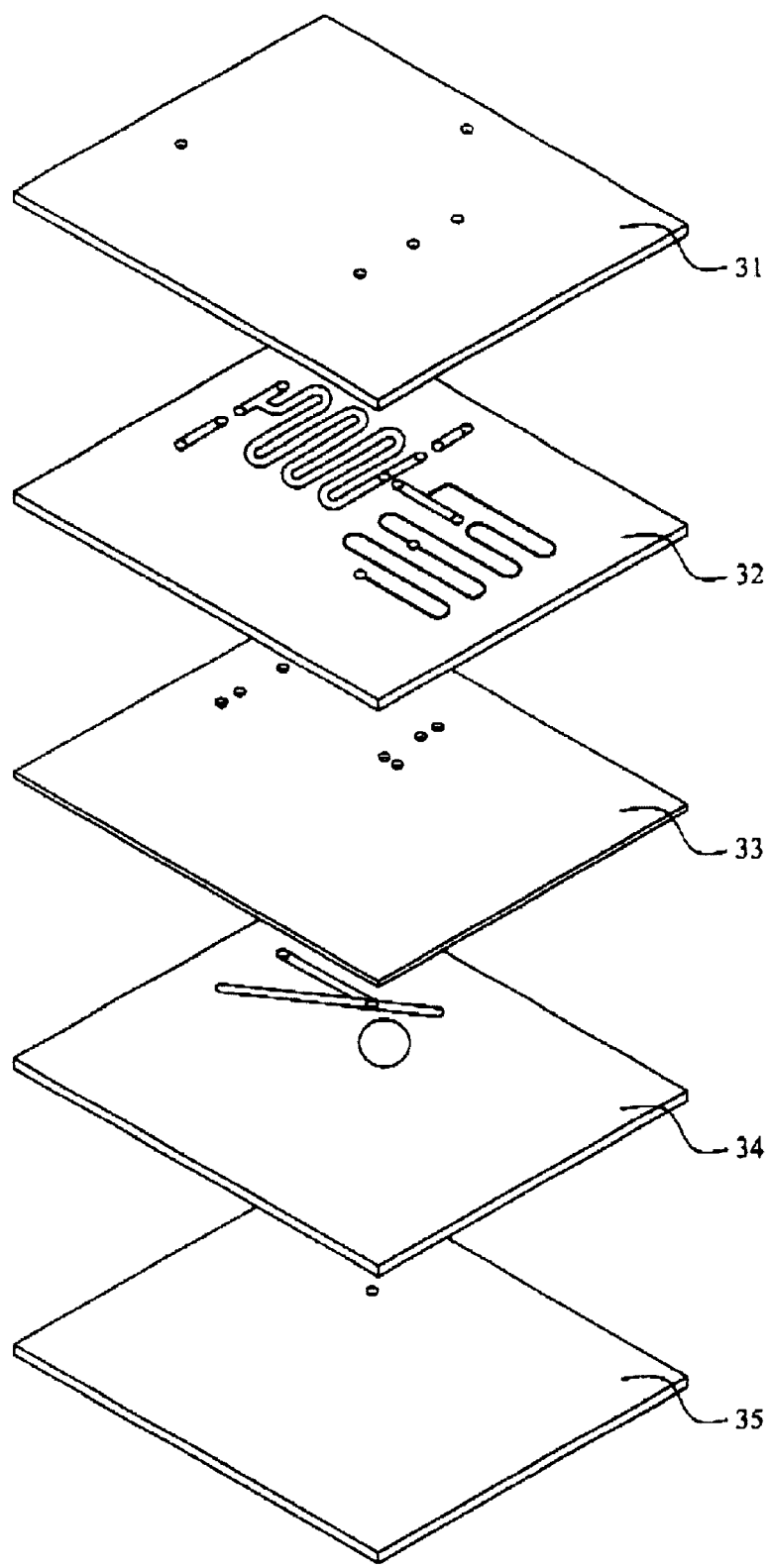
FIG. 3 shows the perspective view of the injection assembly in accordance with the present invention.

Sample injector is confined within the block of bold line. An external solenoid valve is used to control the processes of sampling and injection. The pressurized gas from carrier gas tank 111 is split into a carrier gas tube 112 and a pressurizing tube 113. The carrier gas tube 112 is used for the conventional purpose of carrying sample through capillary column to gas detector. The pressurizing tube 113 is connected to one end of the solenoid valve 114 to control the sampling and injection processes. The other end of the solenoid valve leads to the inlet of pressurizing channel 15. At the normal situation without actuating the solenoid valve (gate closed), inlet valve 21 and outlet valve 22 are open, and sample is drawn into the gas sample channel 11 by a pump (not shown) while carrier gas flows through analytical and reference columns. When the solenoid valve is actuated and gate open, channels are pressurized and inlet valve 21 and outlet valve 22 rendered closed. In the mean time, the injection valve 23 is rendered open so that sample is injected to the analytical capillary column 115 and is carried to a gas detector. Amount of sample injection is controlled by the duration of solenoid valve opening, usually less than 1 second. FIG. 2 shows the micro fabricated view of the injection assembly. There are total of five layers well aligned and bonded together. View is from the top. The perspective view is shown in FIG. 3. It contains five layers 31, 32, 33, 34 and 35 from the top to the bottom.

Figure 4:
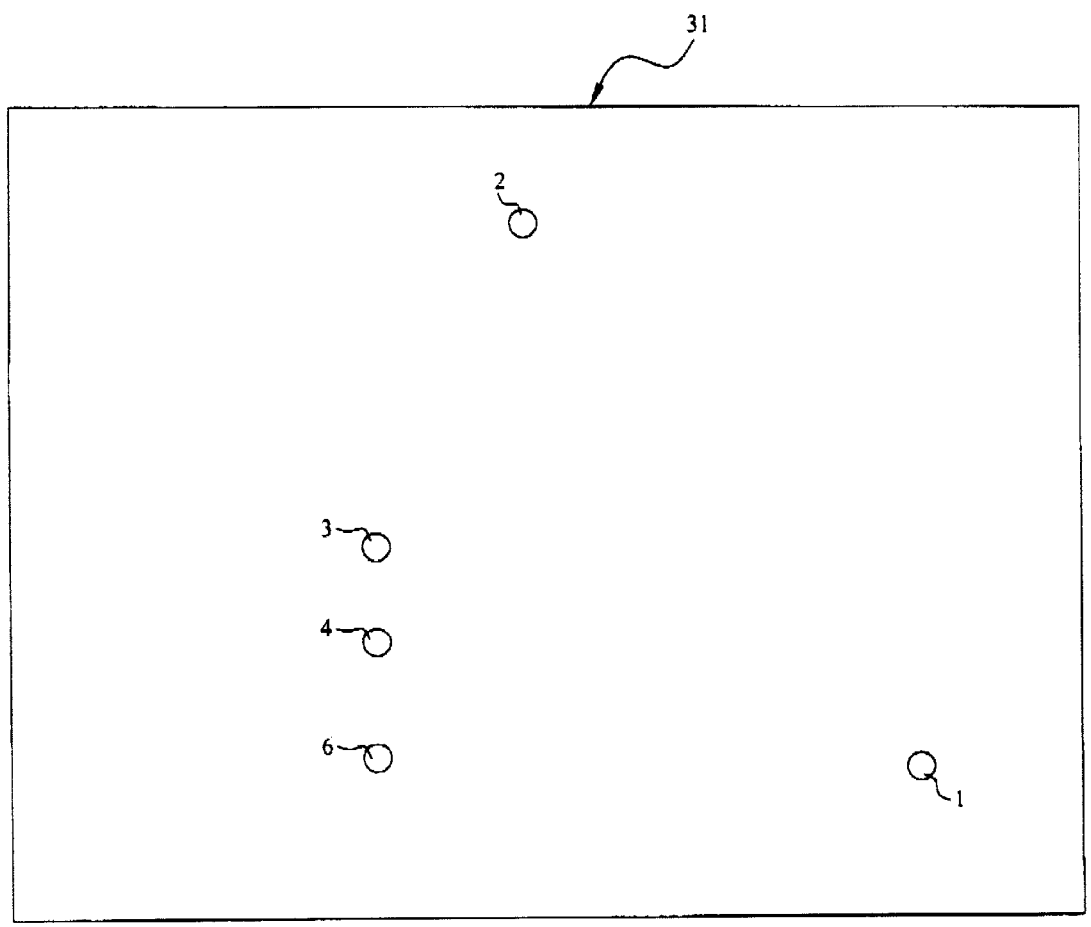
FIG. 4 shows the first layer 31 drilled with five aligned holes in accordance with the present invention.

FIG. 4 shows the first layer 31 etched with five aligned holes. It serves as cover plate and interfacial connection to outside columns. Inlet hole 1 is connected to sample source and introduces sample to the channel 11. Outlet hole 2 connected to a pump is used to draw the sample and clean the channel for next use. Carrier gas port 4 is connected to carrier gas tube 112, and then split into an analytical gas channel 12 and a reference channel 13. Hole 3 is connected to the analytical capillary column 115 and hole 6 is connected to reference capillary column 116. Then, they lead to a common gas detector.

Figure 5:
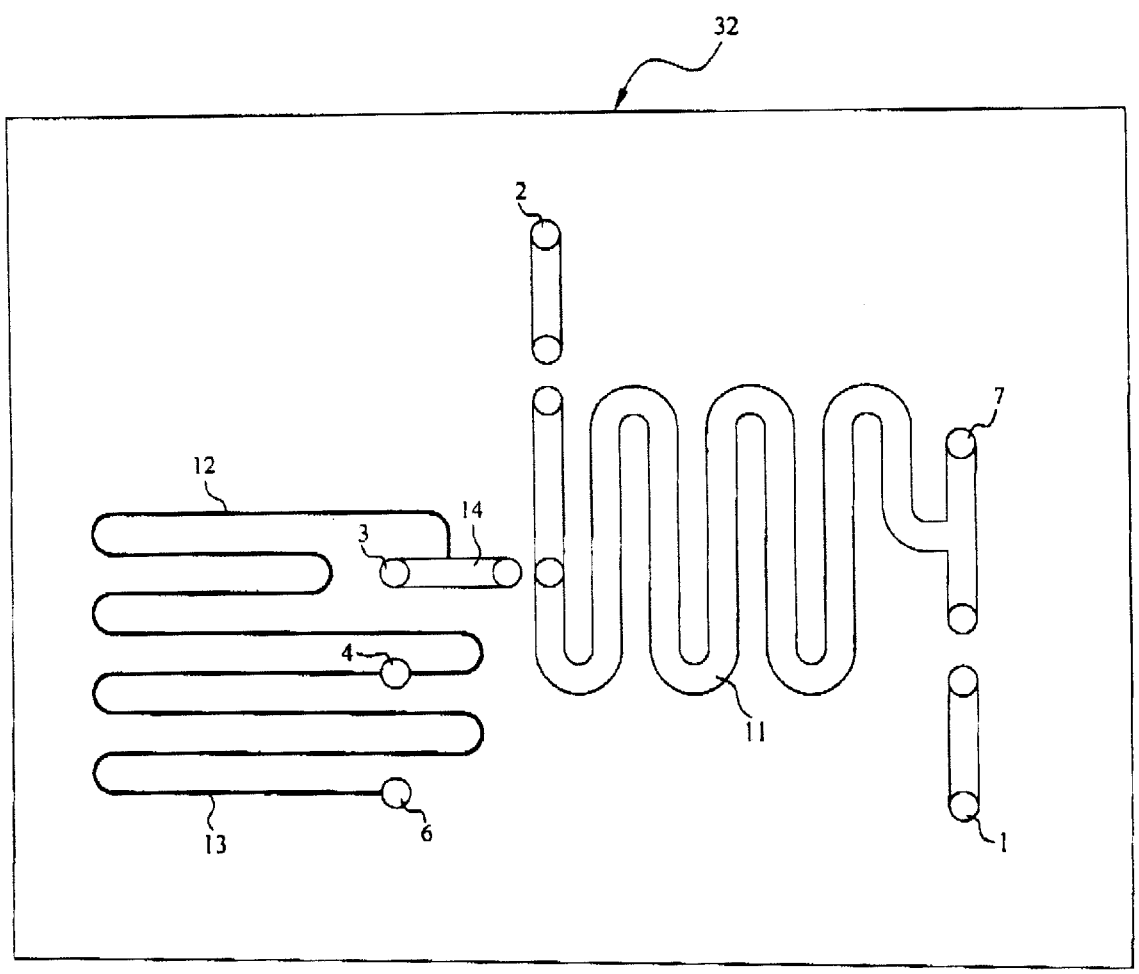
FIG. 5 shows the topside of the second layer 32 in accordance with the present invention.
Figure 6:
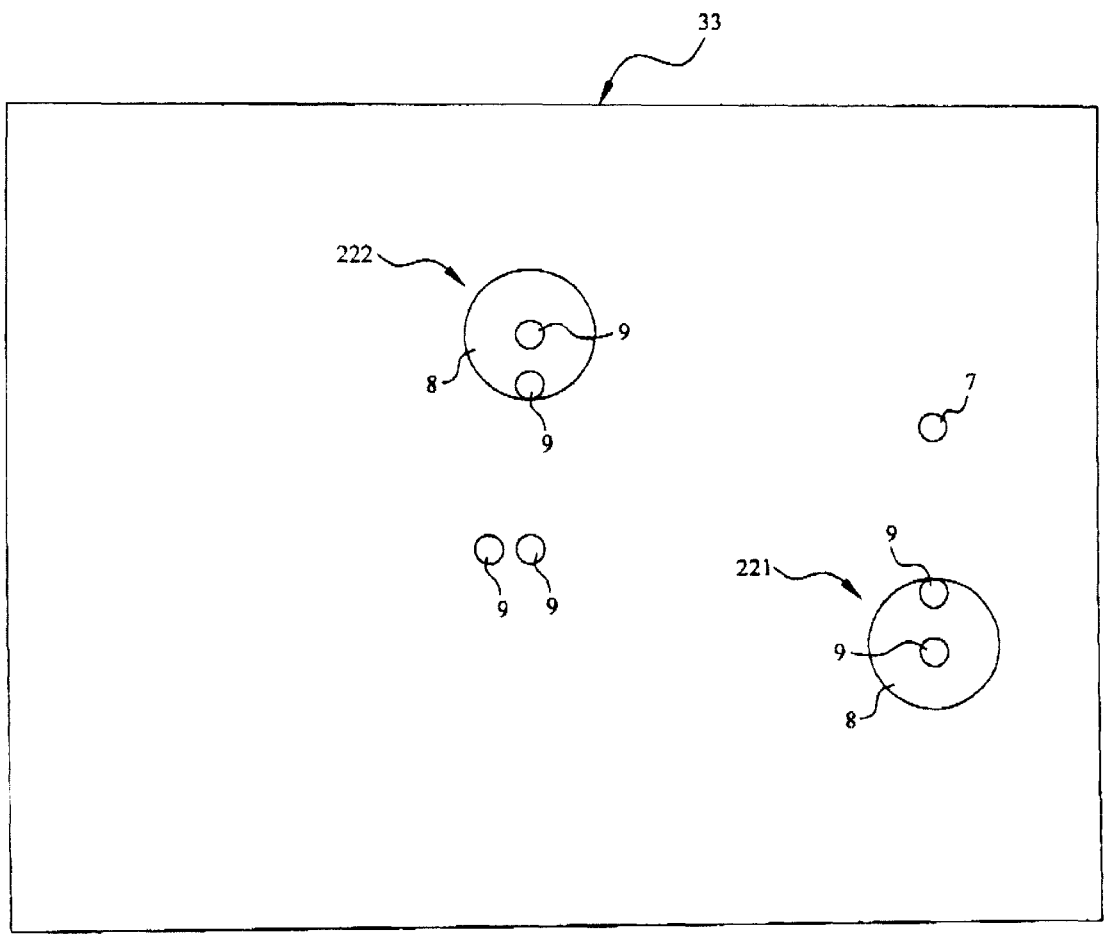
FIG. 6 shows the third layer 33 in accordance with the present invention.

FIG. 5 shows the topside of the second layer 32. It is fabricated with a gas sample channel 11, an analytical gas channel 12, a reference gas channel 13, a gas mix channel 14, and five connecting ports 1, 2, 3, 4 and 6 aligned wit the corresponding holes on the first layer. The analytical gas channel 12 and reference gas channel 13 are much narrower than gas sample channel 11 such that a proper pressure difference is generated between opposing sides of the diaphragm of injection valve 23 upon introduction of pressurizing gas. Channel 12 serves the purpose as a restrictor, and channel 13 is also restricted so that the pressure drop is the same on both columns. A simple calculation from Poiseuille equation supplies a good estimation of pressure drop from reduced channel. FIG. 6 shows the third layer 33. It is fabricated with two valve seats (221, 222) corresponding to inlet valve 21 and outlet valve 22, two passing holes 9 on each valve seat, and a passing hole 7 to let in the pressurizing gas from fourth layer. The third layer (not shown) is a flexible diaphragm with a passing hole 7.

Figure 7:
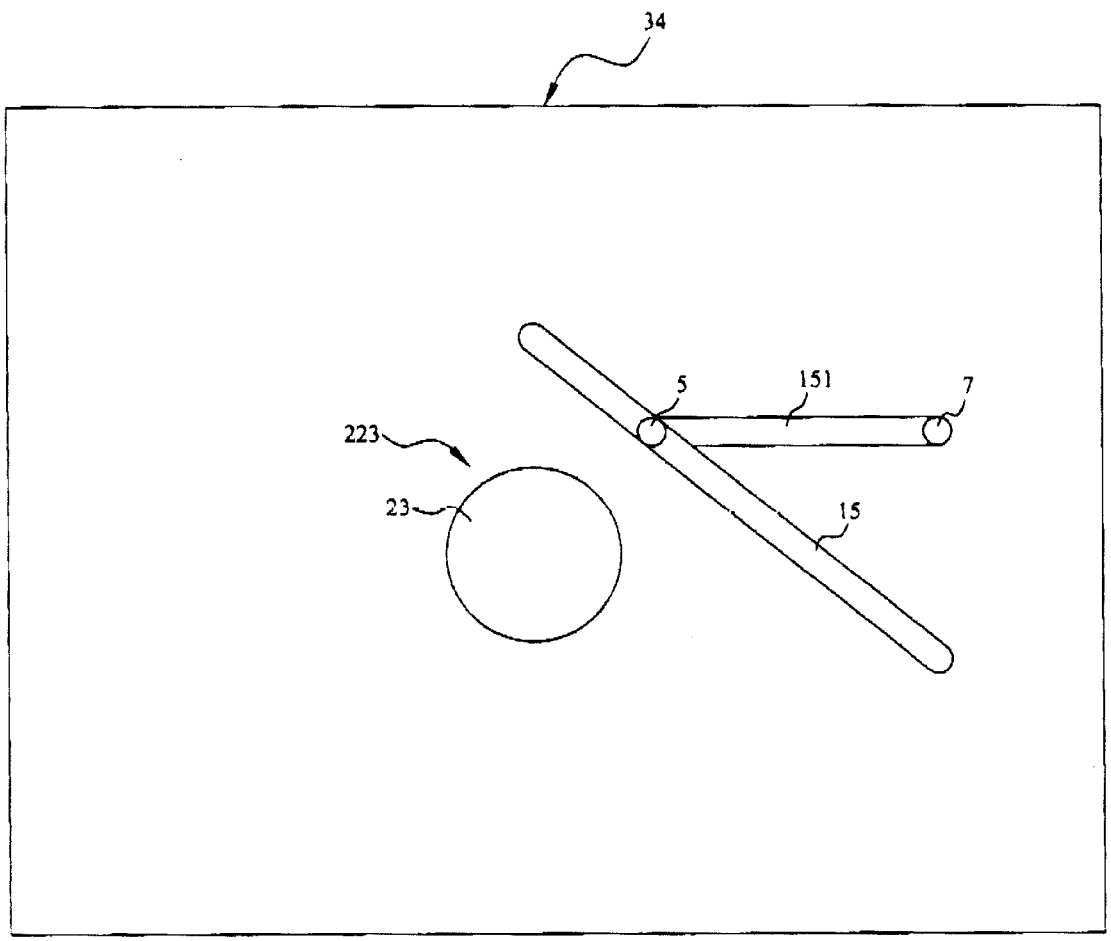
FIG. 7 shows the fourth layer 34 in accordance with the present invention.
Figure 8:
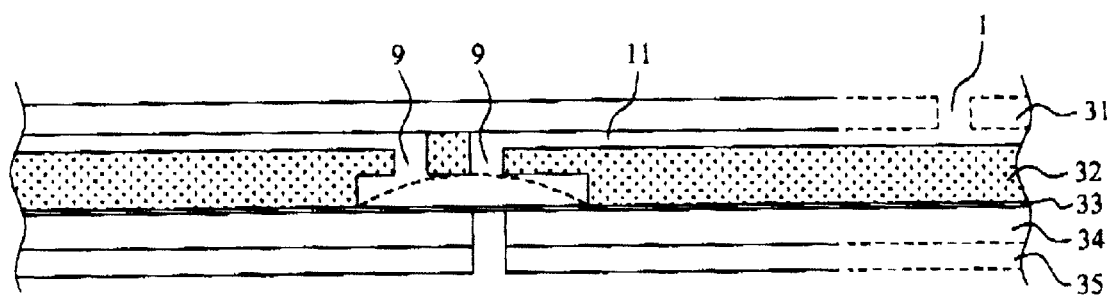
FIG. 8 shows the details of sample inlet valve 21 and outlet valve 22 in accordance with the present invention.
Figure 9:
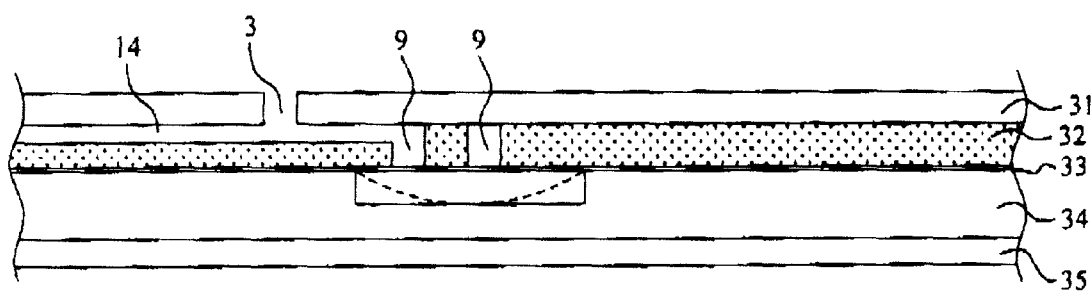
FIG. 9 shows the details of injection valve 23 in accordance with the present invention.

FIG. 7 shows the fourth layer 34. It is fabricated with a pressurizing gas inlet hole 5, pressurizing channel 15 leading to the diaphragms of valve seats 21 and 22, pressurizing channel 151 leading to the diaphragms of valve seat 223 from hole 7 to the gas sample channel 11 on the second layer. FIG. 8 shows the details of sample inlet valve 21 and outlet valve 22. FIG. 9 shows the details of injection valve 23. At the normal situation without actuating the solenoid valve, the flexible diaphragm is flat (solid line 33), therefore sample gas can pass between holes 9 and inlet valve 21 and outlet valve 22 are open. Sample is drawn into the gas sample channel 11 by a pump (not shown). In the mean time, injection valve 23 is closed, and gas In the gas sample channel 11 will not mix with the carrier gas in channels 12 and 14. When the solenoid valve is actuated and gate open, channels are pressurized which leads to the collapse of flexible diaphragm (dashed line 33) on valve seats 221, 222, and 223, and inlet valve 21 and outlet valve 22 rendered closed. In the mean time, the injection valve 23 is rendered open so that a plug of sample is injected to the mixing channel 14 and led to the analytical capillary column 115 and the gas detector. Amount of sample injection is controlled by the duration of solenoid valve opening, usually less than 1 second.

Figure 10:
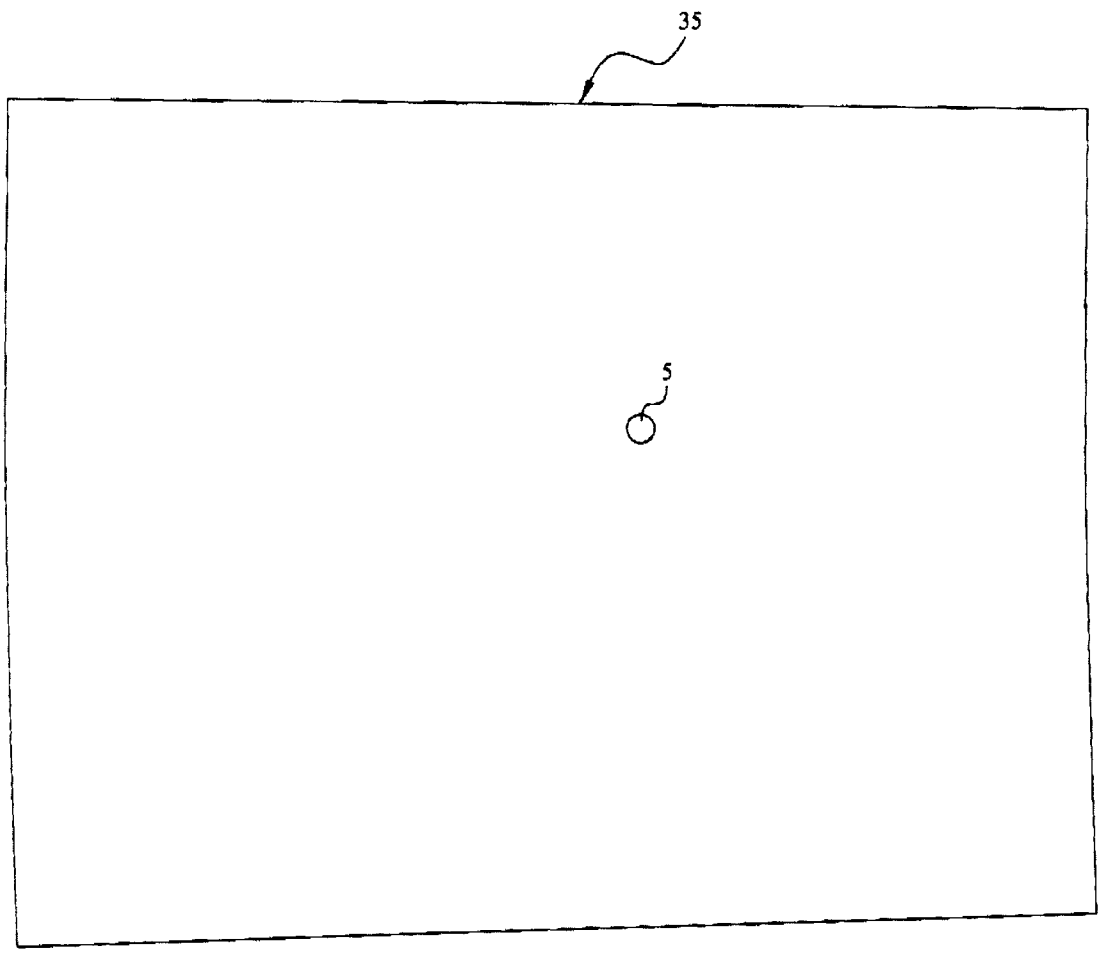
FIG. 10 shows the fifth layer 35 in accordance with the present invention.

FIG. 10 shows the fifth layer. It serves as another cover plate. The pressuring gas inlet port is connected to the pressurizing tube 113 and carrier gas tank 111.

The channels and valve seats on each layer wafer can be fabricated through the conventional photolithographic techniques, The wafers are selected from the group consisting of round shape, rectangular shape or square shape. Masks are made according to the layout design to define the pattern Light sensitive photoresist is coated, and then go through photo exposure, developing and etching processes in this case, silicon or copper sheet can be used as substrate. Another fabrication method of the channels and valve seats is precision micro machining. In this case, polymers such as poly(methylmethacrylate) or polycarbonate is suggested as substrate material for fabrication. Another fabrication method of the channels and valve seats is LIGA processes well developed in micro electromechanic system (MEMS) techniques. In this case, poly(methylmethactylate) or SU-8 photoresist is suggested as substrate material for fabrication. The flexible diaphragm must have the properties of flexible, strength, chemical stability, etc Polymer material such as polyimide, silicon rubber or Kapton (trade name) is suggested for this purpose. They are all commercially available.

All five layers are properly aligned and bonded by adhesives. This assembly forms a sound and workable sample injection device. This sample injection device has the advantage of using only one solenoid valve. Upon activation of the solenoid valve, all three micro valves in the injection device are actuated simultaneously and rendered the injection of sample to the analytical column. The sample channel serves as sample chamber or reservoir. No pre-pressurization is necessary before solenoid valve actuation. Pre-pressurizing the sample chamber for injection will require a pressure of several tens of pounds per square inch. This will risk the leakage of sample through fragile micro valves. In this invention, therefore, leak through the micro valves is not a problem. In the event of leak before sample injection, it is a leak from analytical gas channel 12 to gas sample channel 11. Leak during injection will be from inlet valve 21 and outlet valve 22 to atmosphere. Both situations are not detrimental to gas chromatographic analysis. A test shows that a pressure difference of 3 pounds per square inch, much smaller than the sample pre-pressurization, will property close the inlet valve 21 and outlet valve 22, and open the injection valve 23 This will make fabrication technique much easier.

The foregoing description of the preferred embodiments of the present invention has been provided for the purpose of illustration and description. It is not intended to be exhaustive or to limit the invention to the precise forms. Obviously many modification, variation and simple derivation will now become apparent to the practitioner skilled in the art.

To sum up, the sectional battery structure according to the present invention is easily and conveniently combined. In contract to present battery structure, it is innovation, and obvious to see the function. It is intended that the scope of the invention be defined by the following claims and their equivalents.

What is claimed is:

1. A sample injection device for gas chromatography, comprising:
   a gas sample channel on a side of second layer to connect to inlet valve, outlet valve and injection valve to inject a fixed portion of sample to an analytical column;
   an inlet valve connecting to inlet at a end of said gas sample channel to introduce sample at normally open condition and closed upon pressurization during sample injection;
   an outlet valve connecting to outlet at a end of said gas sample channel to release excess sample at normally open condition and closed upon pressurization during sample injection;
   an injection valve having its seat on one side of a fourth layer to connect near outlet end of said gas sample channel to be closed at normal condition and opened upon pressurization to inject a fixed portion of sample to an analytical column;
   a carrier gas port on a second layer for same side of said gas sample channel to split into an analytical gas channel and a reference gas channel, wherein said analytical gas channel connected to reference capillary column and said reference gas channel connected to analytical capillary column, said analytical gas channel and said reference gas channel leading to a gaseous detector and being much narrower than said gas sample channel;
   a solenoid valve connecting a carrier gas tank and said gas sample channel being activated open to pressurize the said gas sample channel and close the said inlet valve and outlet valve and open the said injection valve.

2. A sample injection device for gas chromatography according to claim 1, wherein said gas sample channel used as sample storage chamber.

3. A sample injection device for gas chromatography according to claim 1, wherein the said inlet valve and outlet valve have their seats fabricated on the other side of the said second layer with two passing holes on each valve seat leading to said gas sample channel.

4. A sample injection device for gas chromatography according to claim 1, wherein said injection valve has its seat on one side of a fourth layer property aligned to the said gas sample channel.

5. A sample injection device for gas chromatography according to claim 1 further comprise a third layer form between said second layer and said fourth layer.

6. A sample injection device for gas chromatography according to claim 1 further comprise a pressuring gas inlet port and channels on the same side of the said fourth layer and leading to valve seats and passing hole of said second layer opposing the third layer.

7. A sample injection device for gas chromatography according to claim 5, wherein said third layer is selected from the group consisting of polyimide, silicon rubber and Kapton and said third layer has a hole aligned to allow pressurizing gas to pass from the pressurizing channel to the sample channel.

8. A sample injection device for gas chromatography according to claim 1, wherein the said carrier gas channels is much narrower than gas sample channel such that a proper pressure difference is generated between opposing sides of an injection valve diaphragm upon pressurizing said gas sample channel.

9. A sample injection device for gas chromatography according to claim 1, wherein said solenoid valve is activated open for a pre-determined short period to inject a fixed amount of sample to said analytical column.

10. A sample injection device for gas chromatography according to claim 1 further comprise an external carrier gas tank being connected to said carrier gas channel via solenoid valve for pressurizing sample storage channel.

11. A sample injection device for gas chromatography according to claim 8 further comprise a pressure so adjusted that the generated pressure difference between opposing sides of the said injection valve diaphragm is useful for valve actuation.

12. A sample injection device for gas chromatography, comprising:
   a first layer on top of thin cover plate with properly aligned holes for gas sample inlet and outlet and carrier gas inlet and outlet;
   a second layer for gas sample channel and gas sample inlet and outlet valve seats
   a third layer serving as valve actuation;
   a fourth layer for pressurizing gas channel and a third valve seat; and
   a fifth layer, on bottom of thin cover plate with properly aligned pressuring gas inlet port for connection to external carrier gas tank and introduction of pressurizing gas.

13. A sample injection device for gas chromatography according to claim 12 further comprise micro lithographic techniques comprising masks, photo resist, photo exposure, developing and etching for channel and valve seat.

14. A sample injection device for gas chromatography according to claim 12, wherein said first wafer, said second wafer, said third wafer and said fourth wafer are selected from the group consisting of round shape, rectangular shape or square shape.

15. A sample injection device for gas chromatography according to claim 12, wherein said first wafer, said second wafer, said third wafer and said fourth wafer are selected from the group consisting of silicon substrate, copper substrate.

16. A sample injection device for gas chromatography according to claim 12 further comprise precision micro machining for channel and valve seat.

17. A sample injection device for gas chromatography according to claim 12, wherein said first wafer, said second wafer said third wafer and said fourth wafer using precision micro machining are selected from the group consisting of poly(methylmethacrylate) substrate and polycarbonate substrate.

18. A sample injection device for gas chromatography according to claim 12 further comprise LIGA processes as in microelectromechanic system techniques for channel and valve seat.

19. A sample injection device for gas chromatography according to claim 12, wherein said first wafer, said second wafer, said third water and said fourth wafer fabricating through LIGA processes as in microelectromechanic system techniques are selected from the group consisting of poly (methylmethacrylate) and SU-8 photoresist.

20. A sample injection device for gas chromatography according to claim 12, wherein said first wafer, said second wafer, said third water and said fourth wafer are aligned and bonded by adhesives.

21. A sample injection device for gas chromatography according to claim 12, wherein said third valve seat is on one side of a pressurizing wafer property aligned to the said gas sample channel.

* * * * *